United States Patent [19]

Otomo et al.

[11] Patent Number: 4,798,913

[45] Date of Patent: Jan. 17, 1989

[54] METHOD FOR SEPARATING A TRIHALOGENOBENZENE ISOMER

[75] Inventors: Kikuo Otomo; Masashi Yamagushi; Masami Ito; Hiroki Tokunaga, all of Tokyo, Japan

[73] Assignee: Hodogaya Chemical Co., Ltd., Tokyo, Japan

[21] Appl. No.: 140,991

[22] Filed: Jan. 5, 1988

[51] Int. Cl.$^4$ .................... C07C 17/38; C07C 25/10
[52] U.S. Cl. ........................ 570/211; 570/190
[58] Field of Search .................. 570/190, 211

[56] References Cited

U.S. PATENT DOCUMENTS

| | | | |
|---|---|---|---|
| 2,725,407 | 11/1955 | Kolka | 570/211 |
| 2,958,708 | 11/1960 | Fleck | 570/211 |
| 4,254,062 | 3/1981 | Wambach | 570/211 |
| 4,571,441 | 2/1986 | Miwa et al. | 570/211 |
| 4,605,799 | 8/1986 | Miwa et al. | 570/211 |
| 4,698,453 | 10/1987 | Miwa et al. | 570/211 |

FOREIGN PATENT DOCUMENTS

| | | | |
|---|---|---|---|
| 0046068 | 2/1982 | European Pat. Off. | 570/190 |
| 0072008 | 2/1982 | European Pat. Off. | 570/202 |
| 0125077 | 11/1984 | European Pat. Off. | 570/211 |
| 0131924 | 8/1983 | Japan | 570/190 |

Primary Examiner—Werren B. Lone
Attorney, Agent, or Firm—Oblon, Fisher, Spivak, McCelland & Maier

[57] ABSTRACT

A method for separating a trihalogenobenzene isomer from a mixture of at least two trihalogenobenzene isomers selected from the group consisting of 1,2,3-, 1,2,4- and 1,3,5-substituted isomers among trihalogenobenzenes represented by the formula:

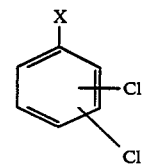

wherein X is Cl or Br, by means of a zeolite adsorber, characterized in that a ZSM-zeolite is used as the adsorber.

10 Claims, No Drawings

METHOD FOR SEPARATING A TRIHALOGENOBENZENE ISOMER

The present invention relates to a method for adsorptive separation of trihalogenobenzene isomers. A trichlorobenzene will be referred to simply as TCB, and a dichlorobromobenzene will be referred to as DCBB.

TCB and DCBB to be separated by the present invention are important as intermediates for agricultural chemicals, dyestuffs and industrial reagents.

TCBs and DCBBs can be obtained by chlorination and bromination, respectively, of dichlorobenzene, followed by isomerization. However, in both cases, the boiling points of the respective isomers are close to one another, and it is very difficult to separate and recover them as individual components by rectification of the mixture of such isomers.

As a method for their separation, it is known to recover 1,3,5-TCB or 3,5-DCBB by crystallization.

Further, Japanese Unexamined Patent Publication No. 219131/1983 discloses a method for adsorptive separation of a mixture of TCB isomers by means of a faujasite type zeolite.

However, with the former method by crystallization, it is difficult to obtain the respective isomers in high purity. On the other hand, the latter adsorptive separation method by means of zeolite requires a desorbing agent and developing agent such as toluene, and it has a drawback that TCB will have to be separated from such an agent by distillation.

Under these circumstances, the present inventors have conducted extensive researches for a method for adsorptive separation of a mixture of trihalogenobenzene isomers. As a result, they have found a catalyst having peculiar characteristics such that it is capable of selectively separating and recovering an isomer substituted at certain specific positions. The present invention has been accomplished on the basis of this discovery.

Namely, the present invention provides a method for separating a trihalogenobenzene isomer from a mixture of at least two trihalogenobenzene isomers selected from the group consisting of 1,2,3-, 1,2,4- and 1,3,5 substituted isomers among trihalogenobenzenes represented by the formula:

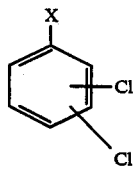

wherein X is Cl or Br, by means of a zeolite adsorber, characterized in that a ZSM-zeolite is used as the adsorber.

Now, the present invention will be described in detail with reference to the preferred embodiments.

The ZSM-zeolite used in the present invention is an adsorber having peculiar characteristics such that the order of the adsorptivity for various isomers substituted at different positions is 1,3,5-substituted isomer 1,2,3-substituted isoomer <<1,2,4-substituted isomer and that the difference in the absorptivity is extremely large as between the 1,2,3- and 1,3,5-substituted isomers and the 1,2,4-substituted isomer.

Accordingly, by using the adsorber of the present invention, it is possible not only to separate the 1,2,4-substituted isomer from a mixture of three isomers of 1,2,3-, 1,3,5- and 1,2,4-substituted TCBs or DCBBs but also to isolate each isomer from a mixture of two isomers such as from a combination of 1,2,3- and 1,2,4-substituted isomers or from a combination of 1,3,5and 1,2,4-substituted isomers.

The ZSM-zeolite to be used in the present invention may be ZSM-5 zeolite as disclosed in Japanese Examined Patent Publication No. 10064/1971 or zeolites belonging to the same category as ZSM-5 zeolite, such as ZSM-8 as disclosed in U.K. Pat. No. 1,334,243, ZSM-11 as disclosed in Japanese Examined Patent Publication No. 23280/1978, ZSM-21 as disclosed in U.S. Pat. No. 4,001,346, ZSM-35 as disclosed in Japanese Unexamined Patent Publication No. 144500/1978, Zeta 1 zeolite as disclosed in Japanese Unexamined Patent Publication No. 67299/1976 and Zeta 3 zeolite as disclosed in Japanese Unexamined Patent Publication No. 67298/1976.

The zeolite used in the present invention is preferably employed in the form of an acid type. As is wellknown, the acid type zeolite is the one having $H+$, $NH_4+$ or a bivalent or higher polyvalent cation such as a rare earth ion as the cation in the zeolite. Such an acid type zeolite can be prepared by having at least a part of alkali metal ions in the zeolite having monovalent alkali metal ions such as sodium ions, ion exchanged with protons, ammonium cations or polyvalent cations.

Further, prior to the use of the zeolite as a catalyst, it is necessary to remove water of crystallization therefrom. Usually, the content of water of crystallization can be substantially reduced at a temperature of 100° C. or higher. Preferably, the zeolite is heated at a temperature of from 300° to 600° C. whereby almost all water of crystallization can be removed.

The zeolite to be used in the present invention may be in the form of a powder or crushed blocks, or may be shaped products obtained by e.g. compression molding, extrusion molding or a molding method by means of mulmelizer. Further, a binder such as bentonite or alumina sol may be added if necessary for the molding. In a small scale operation, the zeolite may be used in a powder form. For an industrial operation, it is preferred to employ a molded product having a spherical shape with a diameter of from 0.1 to 10 mm to avoid a pressure loss. The shape of the zeolite may be suitably selected depending upon the particular apparatus.

There is no particular restriction as to the $SiO_2/Al_2O_3$ ratio. However, the ratio is preferably within a range of from 10 to 200.

For the operation of the method of the present invention, a batch method using a conventional fixed bed system or a continuous method may be used for the separation step. However, in a small scale operation, the batch method is advantageously used since the apparatus is simple and the operation is easy.

The separation step of the present invention may be carried out basically by a cycle of adsorption-washing-desorption-regeneration of the adsorber, with one or more adsorption chambers (packed with the adsorber).

Namely, a mixture of trihalogenobenzene isomers is contacted in an adsorption chamber with the adsorber of the present invention, whereby the non-adsorbed component and the adsorbed component are selectively separated.

The adsorption of the present invention may be conducted at a temperature from room temperature to 350°

C. preferably from 100° to 250° C. If the temperature exceeds 350° C., a side reaction such as an isomerization reaction of trihalogenobenzenes is likely to take place, such being undesirable. The adsorption is conducted usually under a pressure of from atmospheric pressure to about 50 kg/cm², preferably from atmospheric pressure to about 30 kg/cm² Further, a substance which does not adversely affect the adsorption and desorption may be added to the mixture of trihalogenobenzene isomers as a diluting solvent at the time of the adsorption.

There is no particular restriction as to the manner of desorbing the trihalogenobenzene isomer adsorbed by the adsorptive separation of the present invention. However, desorption by steam is preferred.

Now, the present invention will be described in further detail with reference to Examples. However, it should be understood that the present invention is by no means restricted by such specific Examples.

REFERENCE EXAMPLE 1

A powder of ZSM-5 type zeolite comprising 90.1% by weight of $SiO_2$, 6.1% by weight of $Al_2O_3$ and 3.8% by weight of $Na_2O$ with a $SiO_2/Al_2O_3$ ratio of 25.1, was prepared in accordance with the process of Example 1 of Japanese Examined Patent Publication No. 10064/1971. Then, the zeolite powder was subjected to ion exchange treatment five times by using an aqueous solution containing 10% by weight of ammonium nitrate (solid-liquid ratio: 2.0 liter/kg, 95° C.), thoroughly washed with water, dried at 150° for 5 hours, and then calcined at 500° for 3 hours to obtain a H-ZSM-5 type zeolite powder. From the X-ray analysis, this H-ZSM-5 type zeolite, was found to be the same as the H-ZSM-5 manufactured by Mobil Oil Corp.

REFERENCE EXAMPLE 2

A ZSM-11 type zeolite powder was prepared in accordance with the Examples of Japanese Examined Patent Publication No. 23280/1978. The zeolite powder was further treated in the same manner as in Reference Example 1 to obtain a H-ZSM-11 type zeolite powder.

EXAMPLE 1

8.2 g of the H-ZSM-5 type zeolite powder of Reference Example 1 was packed in a metal column having an inner diameter of 9.8 mm and a length of 16.3 cm, and a mixture of 1,2,3- and 1,2,4-TCB isomers heated and melted at about 45° C. was introduced under a nitrogen pressure of 2 kg/cm² at 200° C. at a rate of 50 μl/min. The mixture of TCB isomers introduced had a composition of 1,2,3-TCB/1,2,4-TCB =37/70 by weight ratio.

The effluent from the outlet of the column was sampled at a predetermined interval (at an interval of from 3 to 7 minutes), and the amount of the effluent was measured and the composition of the effluent was analyzed by gas chromatography. The effluent sampled upon expiration of about 25 minutes from the initiation of the elution had substantially the same composition as that of the influent, thus indicating the break through point. The change in the composition of the effluent up to the break through point was as shown in Table 1.

Then, nitrogen gas was introduced at the same temperature under a pressure of 2 kg/cm2 for 20 minutes to discharge and wash the attached mixture of TCB isomers.

Then, into the column, a gas mixture of steam (molar fraction: 0.33) and nitrogen (molar fraction: 0.67) was introduced at the same temperature under a pressure of 6 kg/cm² at a rate of 60 ml/min. The adsorbed TCB was desorbed and eluted together with water, and the elution of TCB was completed upon expiration of about 40 minutes. The total effluent of TCB by desorption was 530.2 mg, and the total effluent was analyzed by gas chromatography, whereby 1,2,4-TCB was found to constitute 97.6%.

The apparent adsorption capacity f' of 1,2,4-TCB per unit amount (g) of zeolite is represented by the following formula:

$$f'(\%) = \frac{A(g) \times B(\%)}{\text{Amount of zeolite used (g)}}$$

A: Amount (g) of TCB eluted in the desorption step
B: Concentration (%) of 1,2,4-TCB component in the desorbed liquid.

The apparent adsorption capacity of f' in this Example was 6.31%.

TABLE 1

| | Adsorption step | | | |
|---|---|---|---|---|
| Sample No. | Amount of effluent sampled (mg) | 1,2,3-TCB concentration (%) | 1,2,4-TCB concentration (%) | Note |
| 1 | 65.3 | 83.2 | 16.8 | |
| 2 | 66.7 | 95.3 | 4.7 | |
| 3 | 86.7 | 97.8 | 2.1 | |
| 4 | 73.3 | 99.2 | 0.8 | |
| 5 | 60.0 | 99.2 | 0.8 | |
| 6 | 98.5 | 76.1 | 23.9 | |
| 7 | 190.2 | 28.9 | 71.1 | |
| | Total: 640.7 | 72.6 | 27.4 | Total amount (mg) and composition (%) of effluent up to the break through point |
| | Desorption step | | | |
| 8 | 530.2 | 2.4 | 97.6 | f' = 6.31% |

EXAMPLES 2 to 4

Into the column used in Example 1, nitrogen gas was introduced at 200° C. under a pressure of 6 kg/cm² at a rate of 40 ml/min for two hours to dry and regenerate the adsorber.

Upon completion of the regeneration, the same cycle of adsorption-washing-desorption-regeneration as in Example 1 was repeated 4 times including the cycle of Example 1. The amount and the composition of the non-adsorbed effluent up to the break through point and the amount and the composition of the effluent in the desorption step and the apparent adsorption capacity f' are shown in Table 2.

Further, the crystallinity of the zeolite after repeating the cycle 4 times, was analyzed by X-ray analysis, whereby no destruction of the crystal structure was observed.

EXAMPLE 5

The adsorption-washing-desorption-regeneration operation was conducted in the same manner by using the same apparatus as in Example 1 except that the H-ZSM-5 type zeolite used in Example 1 was changed to the H-ZSM-11 type zeolite prepared in Reference Example 2. The results are shown in Table 2.

TABLE 2

| | Adsorption step | | | Desorption step | | | |
|---|---|---|---|---|---|---|---|
| Example No. | Total effluent up to the break through point (mg) | 1,2,3-TCB concentration (%) | 1,2,4-TCB concentration (%) | Total effluent (mg) | 1,2,3-TCB concentration (%) | 1,2,4-TCB concentration (%) | Apparent adsorption capacity f' (mg) |
| 1 | 640.7 | 72.6 | 27.4 | 530.2 | 2.4 | 97.6 | 6.31 |
| 2 | 527.3 | 79.7 | 20.3 | 515.4 | 1.8 | 98.2 | 6.17 |
| 3 | 563.2 | 78.1 | 21.9 | 541.2 | 2.0 | 98.0 | 6.47 |
| 4 | 600.9 | 74.2 | 25.8 | 533.3 | 2.1 | 97.9 | 6.37 |
| 5 | 543.8 | 68.8 | 31.2 | 500.1 | 2.7 | 97.3 | 5.93 |

EXAMPLE 6

The adsorption-washing-desorption-regeneration operation was conducted in the same manner by using the same apparatus as in Example 1 except that the influent material was changed to a mixture of 1,3,5- and 1,2,4-TCB isomers with the composition being 1,3,5-TCB/1,2,4-TCB =30/70 by weight ratio. The change in the composition was analyzed in the same manner as in Example 1, and the results are shown in Table 3.

TABLE 3

| | Adsorption step | | | |
|---|---|---|---|---|
| Sample No. | Amount of effluent sampled (mg) | 1,3,5-TCB concentration (%) | 1,2,4-TCB concentration (%) | Note |
| 1 | 52.7 | 93.0 | 7.0 | |
| 2 | 42.0 | 95.2 | 4.8 | |
| 3 | 47.3 | 99.1 | 0.9 | |
| 4 | 57.3 | 98.3 | 1.7 | |
| 5 | 102.7 | 53.1 | 46.9 | |
| 6 | 180.7 | 30.2 | 69.8 | |
| | Total: 482.7 | 62.4 | 37.6 | Total amount (mg) and composition (%) of effluent up to the break through point |
| | Desorption step | | | |
| 8 | 528.4 | 0.9 | 99.1 | f' = 6.39% |

EXAMPLE 7

The adsorption-washing-desorption-regeneration operation was conducted in the same manner by using the same apparatus as in Example 1 except that the influent material was changed to a mixture of 1,3,5- and 1,2,3-TCB isomers with the composition being 1,3,5-TCB/1,2,3-TCB =35/65 by weight ratio. The change in the composition was analyzed in the same manner as in Example 1, and the results are shown in Table 4.

In this case, 1,2,3-TCB is the strongly adsorbed component, and the value for B in the calculation of the apparent adsorption capacity f' is the concentration (%) of 1,2,3-TCB component in the desorbed liquid.

TABLE 4

| | Adsorption step | | | |
|---|---|---|---|---|
| Sample No. | Amount of effluent sampled (mg) | 1,3,5-TCB concentration (%) | 1,2,3-TCB concentration (%) | Note |
| 1 | 6.0 | 73.2 | 26.8 | |
| 2 | 30.7 | 70.1 | 29.9 | |
| 3 | 59.3 | 58.9 | 41.1 | |
| 4 | 71.3 | 48.8 | 51.1 | |
| 5 | 138.0 | 37.7 | 62.3 | |

TABLE 4-continued

| | Adsorption step | | | |
|---|---|---|---|---|
| Sample No. | Amount of effluent sampled (mg) | 1,3,5-TCB concentration (%) | 1,2,3-TCB concentration (%) | Note |
| | Total: 305.3 | 48.4 | 51.6 | |
| | Desorption step | | | |
| 6 | 360.1 | 16.8 | 83.2 | f' = 3.65% |

EXAMPLE 8

The adsorption-washing-desorption-regeneration operation was conducted in the same manner by using the same apparatus as in Example 1 except that the influent material was changed to a mixture of 3,5- and 2,4-DCBB isomers with the composition being 3,5-DCBB/2,4-DCBB =35/65 by weight ratio. The change in the composition was analyzed in the same manner as in Example 1, and the results are shown in Table 5.

In this case, 2,4-DCBB is the strongly adsorbed component, and the value for B in the calculation of the apparent adsorption capacity f' is the concentration (%) of 2,4-DCBB component in the desorbed liquid.

TABLE 5

| | Adsorption step | | | |
|---|---|---|---|---|
| Sample No. | Amount of effluent sampled (mg) | 3,5-DCBB concentration (%) | 2,4-DCBB concentration (%) | Note |
| 1 | 88.0 | 98.1 | 1.9 | |
| 2 | 44.7 | 99.2 | 0.8 | |
| 3 | 62.7 | 99.4 | 0.6 | |
| 4 | 57.3 | 98.9 | 1.1 | |
| 5 | 52.6 | 98.7 | 1.3 | |
| 6 | 140.7 | 49.9 | 50.1 | |
| 7 | 228.7 | 37.8 | 62.8 | |
| | Total: 674.7 | 67.9 | 33.1 | Total amount (mg) and composition (%) of effluent up to the break through point |
| | Desorption step | | | |
| 8 | 490.0 | 0.8 | 99.2 | f' = 5.93% |

EXAMPLE 9

The adsorption-washing-desorption-regeneration operation was conducted in the same manner by using the same apparatus as in Example 1 except that the influent material was changed to a mixture of 3,5-, 2,6- and 2,4-DCBB isomers with the composition being 3,5-DCBB/2,6-DCBB/2,4-DCBB =60/10/30 by weight ratio. The change in the composition was analyzed in the same manner as in Example 1, and the results are shown in Table 6.

In this case, 2,4-DCBB is the most strongly adsorbed component, and the value for B in the calculation of the apparent adsorption capacity f' is the concentration (%) of 2,4-DCBB component in the desorbed liquid.

TABLE 6

| Sample No. | Adsorption step | | | | Note |
|---|---|---|---|---|---|
| | Amount of effluent sampled (mg) | 3,5-DCBB concentration (%) | 2,6-DCBB concentration (%) | 2,4-DCBB concentration (%) | |
| 1 | 33.3 | 97.8 | 2.0 | 0.2 | |
| 2 | 28.7 | 98.4 | 1.1 | 0.5 | |
| 3 | 43.3 | 93.9 | 6.0 | 0.1 | |
| 4 | 106.0 | 93.5 | 6.3 | 0.2 | |
| 5 | 80.7 | 90.9 | 9.0 | 0.1 | |
| 6 | 118.7 | 90.0 | 9.3 | 0.7 | |
| 7 | 113.3 | 89.5 | 10.2 | 0.3 | |
| 8 | 124.0 | 89.9 | 10.0 | 0.1 | |
| 9 | 76.7 | 88.7 | 10.0 | 1.3 | |
| 10 | 11.3 | 58.1 | 10.9 | 31.0 | |
| Total: | 736.0 | 90.8 | 8.3 | 0.9 | Total amount (mg) and composition (%) of effluent up to the break through point |
| Desorption step | | | | | |
| 11 | 421.1 | 3.1 | 1.1 | 95.8 | f' = 4.92% |

According to the method of the present invention a mixture of trihalogenobenzene isomers (TCBs or DCBBs) with different substitution modes is subjected to adsorptive separation by means of a ZSM-type zeolite, whereby a highly pure trihalogenobenzene can be obtained in an industrially advantageous manner, which used to be hardly possible to accomplish. The ZSM-type zeolite employed can be reused for a long period of time. Thus, the method of the present invention is very advantageous.

We claim:

1. A method for separating a trihalogenobenzene isomer from a mixture of at least two trihalogenobenzene isomers selected from the group consisting of 1,2,3-, 1,2,4- and 1,3,5-substituted isomers among trihalogenobenzenes represented by the formula:

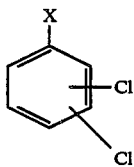

wherein X is Cl or Br, by means of a zeolite adsorber, characterized in that a ZSM-zeolite is used as the adsorber.

2. The method according to claim 1, wherein the ZSM-zeolite is selected from the group consisting of ZSM-5 zeolite, ZSM-8 zeolite, ZSM-11 zeolite, ZSM-21 zeolite, ZSM-35 zeolite, Zeta 1 zeolite and Zeta 3 zeolite.

3. The method according to claim 1, wherein a 1,2,4-trihalogenobenzene is separated from a mixture of 1,2,3-, 1,2,4- and 1,3,5-trihalogenobenzenes, from a mixture of 1,2,3- and 1,2,4-trihalogenobenzenes, or from a mixture of 1,2,4- and 1,3,5-trihalogenobenzenes.

4. The method according to claim 3, wherein the 1,2,3-, 1,2,4- and 1,3,5-trihalogenobenzenes are 1,2,3-, 1,2,4- and 1,3,5-trichlorobenzenes, respectively.

5. The method according to claim 3, wherein the 1,2,3-, 1,2,4- and 1,3,5-trihalogenobenzenes are 2,6-, 2,4- and 3,5-dichlorobromobenzenes, respectively.

6. The method according to claim 1, wherein the ZSM-zeolite is of an acid type.

7. The method according to claim 1, wherein the ZSM-zeolite is a molded product having a spherical shape with a diameter of from 0.1 to 10 mm.

8. The method according to claim 1, wherein the ratio in the ZSM-zeolite is from 10 to 100.

9. The method according to claim 1, wherein the adsorption is conducted at a temperature of from room temperature to 350° C.

10. The method according to claim 1, wherein the adsorption is conducted at a pressure of from atmospheric pressure to about 50 kg/cm².

* * * * *